(12) United States Patent
Mourey et al.

(10) Patent No.: US 9,651,407 B2
(45) Date of Patent: May 16, 2017

(54) CONFIGURABLE SENSOR ARRAYS

(75) Inventors: Devin Alexander Mourey, Corvallis, OR (US); Randy L. Hoffman, Corvallis, OR (US); James William Stasiak, Lebanon, OR (US); Brad Benson, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 563 days.

(21) Appl. No.: 14/240,282

(22) PCT Filed: Sep. 12, 2011

(86) PCT No.: PCT/US2011/051184
§ 371 (c)(1),
(2), (4) Date: Feb. 21, 2014

(87) PCT Pub. No.: WO2013/039468
PCT Pub. Date: Mar. 21, 2013

(65) Prior Publication Data
US 2014/0283630 A1    Sep. 25, 2014

(51) Int. Cl.
*G01D 11/00* (2006.01)
*G01N 27/12* (2006.01)

(52) U.S. Cl.
CPC ........... *G01D 11/00* (2013.01); *G01N 27/122* (2013.01); *Y10T 29/49002* (2015.01)

(58) Field of Classification Search
CPC .... G01R 27/00; G01R 27/2605; G01N 27/00; G01N 27/02; G01N 27/04; G01D 11/00
USPC ........................................ 324/600, 658, 691
See application file for complete search history.

(56) References Cited

U.S. PATENT DOCUMENTS

| 5,678,448 | A | 10/1997 | Fullen et al. |
|---|---|---|---|
| 6,771,208 | B2 | 8/2004 | Lutter et al. |
| 2005/0073324 | A1* | 4/2005 | Umeda |
| 2007/0132342 | A1 | 6/2007 | Walter |
| 2008/0121045 | A1 | 5/2008 | Cole et al. |
| 2009/0166411 | A1 | 7/2009 | Kramer et al. |
| 2009/0195394 | A1* | 8/2009 | Johnson |
| 2010/0239133 | A1 | 9/2010 | Schmitt et al. |

(Continued)

FOREIGN PATENT DOCUMENTS

| CH | EP 1607739 A1 * | 12/2005 |
|---|---|---|
| WO | WO-9953328 | 10/1999 |
| WO | WO-2011082178 | 7/2011 |

OTHER PUBLICATIONS

Desmulliez et al., Intelligent Multi-sensor Arrays for Aircraft Wiring Systems Monitoring, NoE Patent-DfMM, Nov. 2007, 58 pgs.

(Continued)

*Primary Examiner* — Walter L Lindsay, Jr.
*Assistant Examiner* — Milton Gonzalez
(74) *Attorney, Agent, or Firm* — Brooks, Cameron & Huebsch, PLLC

(57) ABSTRACT

Systems, devices, and methods for configurable sensor arrays are provided. An example of a configurable sensor array includes a plurality of sensors in a matrix array formed on a single backplane and a plurality of elements within one of the plurality of sensors, where the plurality of elements provides alternative electrical paths enabling the one of the plurality of sensors to have a range of output impedances.

11 Claims, 5 Drawing Sheets

(56) References Cited

U.S. PATENT DOCUMENTS

2010/0248973 A1 9/2010 Van Lankvelt et al.
2011/0164013 A1 7/2011 Nakagawa et al.

OTHER PUBLICATIONS

Someya et al., Conformable, flexible, large-area networks of pressure and thermal sensors with organic transistor active matrixes, PNAS, Aug. 30, 2005, 12321-12325, vol. 102, No. 35.
Williams et al., Integration Method Delivers Yield Improvements, Space Savings in Sensor Arrays, Jan. 20, 2009, http://spie.org/x33120.xml?pf=true&ArticleID=x33120.

* cited by examiner

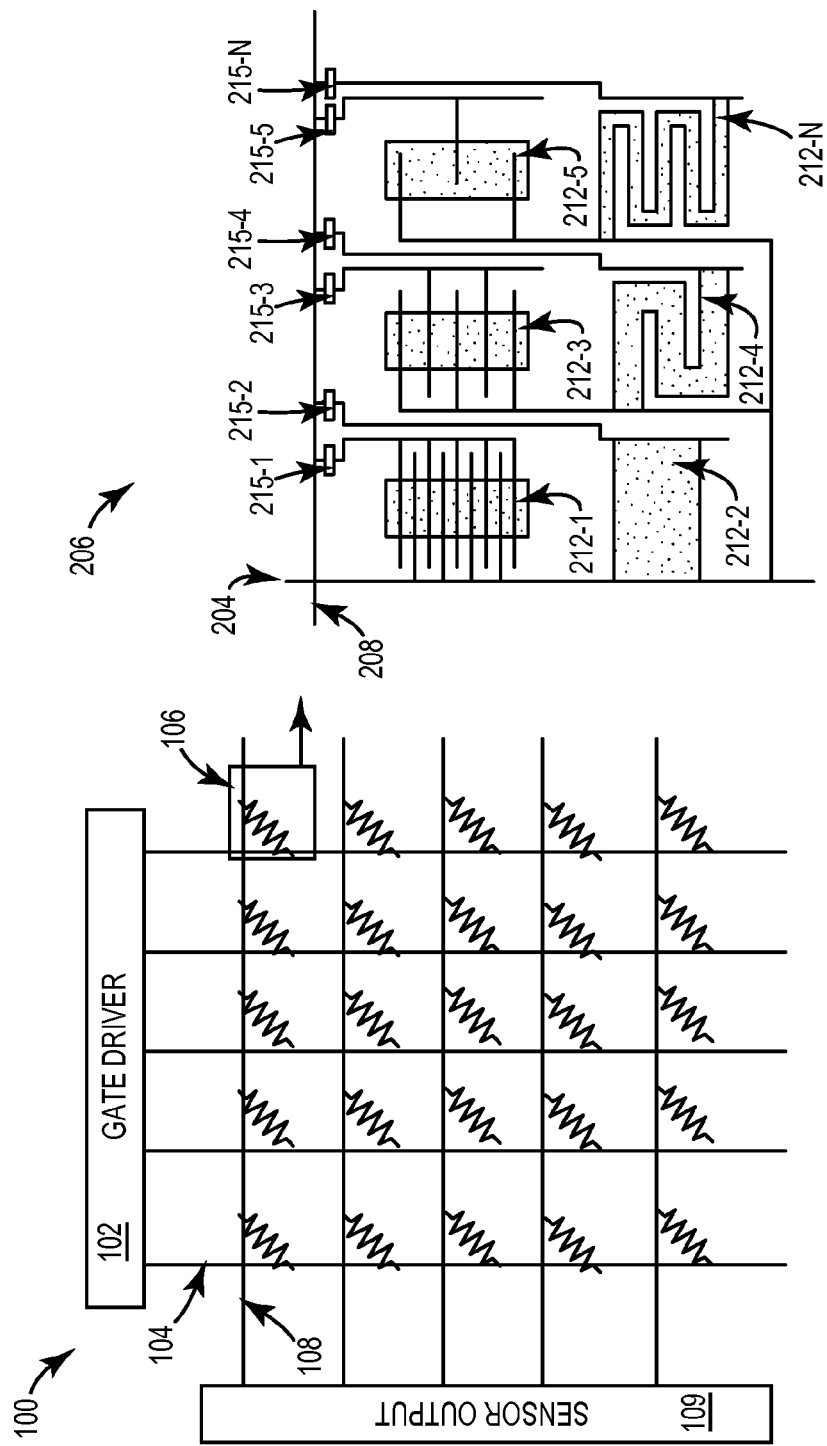

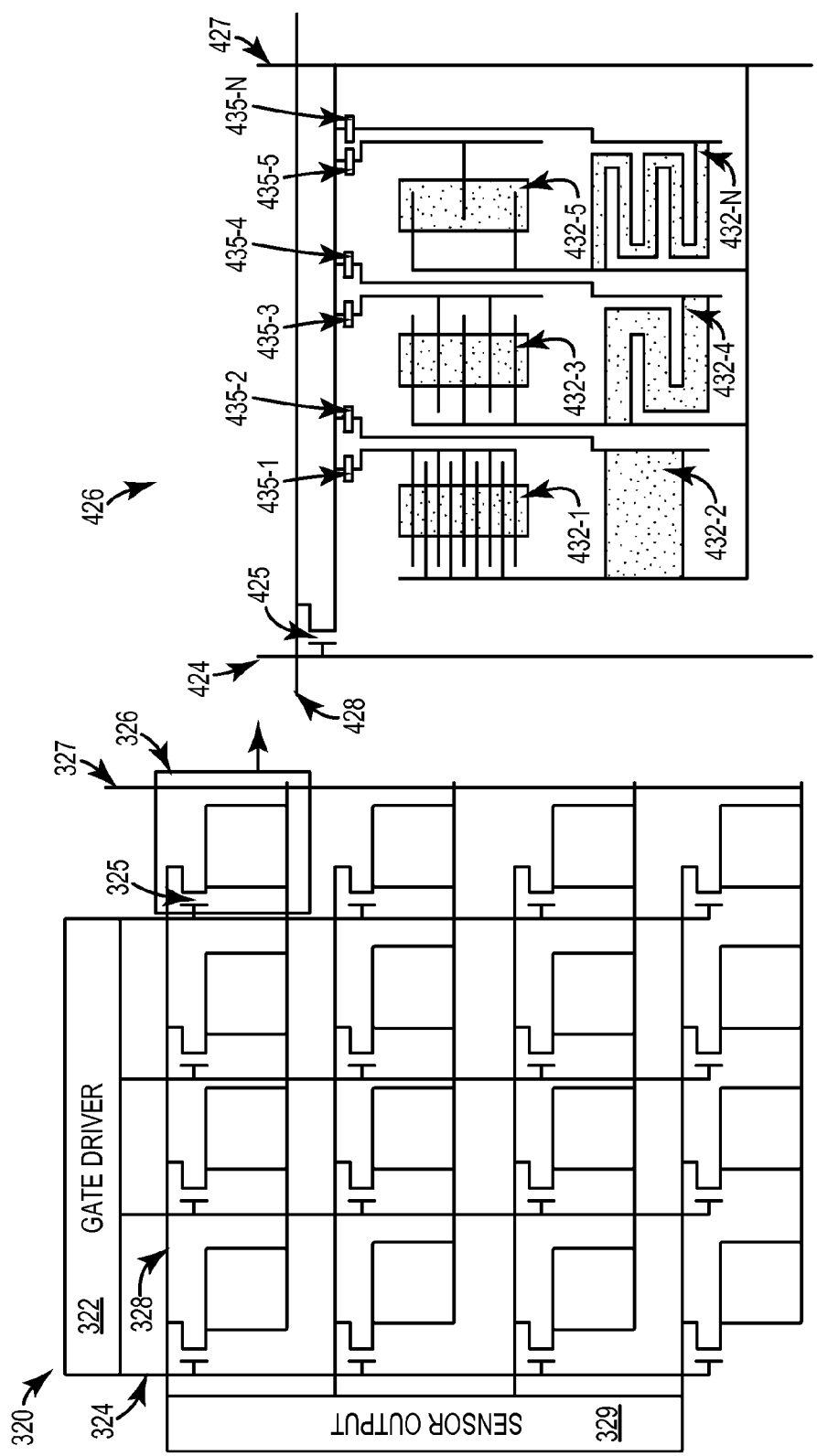

CONFIGURABLE SENSOR ARRAYS

BACKGROUND

Thin film sensor technologies may have a number of applications, for instance, for detecting and/or monitoring temperature, humidity, light, pressure, magnetism, and chemicals, etc. For instance, as-fabricated resistive thin film sensor materials may span a range of electrical resistance from less than 1 ohm (e.g., measured in thousandths of an ohm or mΩ) to greater than 100 million ohms (e.g., measured in millions of ohms or MΩ). As a result, individually customized sensor electrode configurations and/or readout electronics may be used for each sensor or each group of a particular type of sensor, depending on the resistance range of each sensor or each group of a particular type of sensor in a given application thereof relative to input voltage ranges of particular readout electronics.

Production of a custom array with custom readout electronics for each sensor or each group of the particular type of sensor may be expensive per unit unless the product is usable as such, and is purchased, by a large number of downstream customers for the supported application.

BRIEF DESCRIPTION OF THE DRAWINGS

FIG. 1 illustrates an example of a passive matrix of a configurable sensor array according to the present disclosure.

FIG. 2 illustrates an example of a plurality of elements within one of the sensors of a passive matrix of a configurable sensor array according to the present disclosure.

FIG. 3 illustrates an example of an active matrix of a configurable sensor array according to the present disclosure.

FIG. 4 illustrates an example of a plurality of elements within one of the sensors of an active matrix of a configurable sensor array according to the present disclosure.

DETAILED DESCRIPTION

Figure 5:
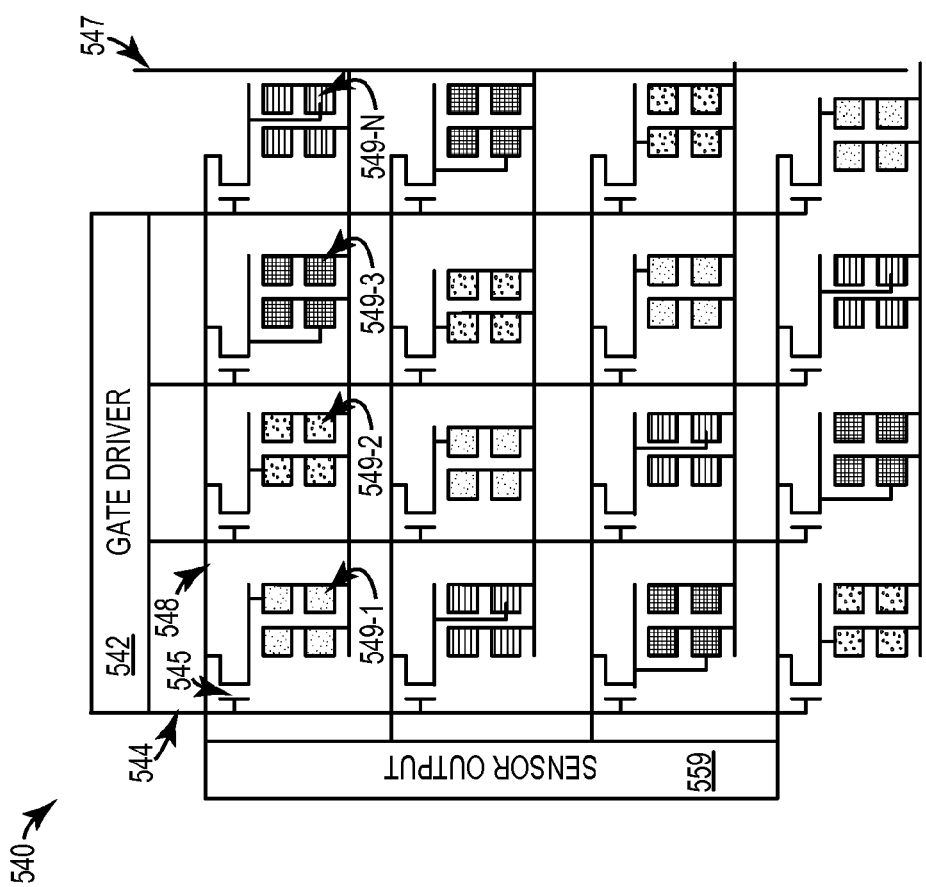
FIG. 5 illustrates an example implementation of a plurality of elements within each of a plurality of different types of sensors of an active matrix of a configurable sensor array according to the present disclosure.

As sensor devices decrease in size and increase in complexity, the ability to detect and/or monitor multiple agents (e.g., sources of input) becomes more desirable, albeit challenging. Sensor devices are usable in many applications, such as DNA analysis, electrophoresis, cell cytometry, chemistry, fuel cells, magnetism, optics, pressure, acoustics, temperature, and humidity, among other applications. However, as useful as these devices may be, they may be "black box" systems, in that a user may have little knowledge of how or where one or more agents being detected and/or monitored are positioned.

This may not matter for single sensor devices. However, as devices are scaled up into large arrays, positioning of detection, routing, etc., may become significant issues. A system capable of positioning detection of input may depend on an ability to create large arrays of sensors capable of detecting the position of agents throughout the array. Such sensor arrays should be easy to fabricate and integrate with available readout devices.

Electrical sensors can meet the desired criteria for a sensor array system as described above because, among other considerations, electrical sensors can be incorporated directly onto a backplane (e.g., a substrate) of a given array because the electrical sensors can be thin, among other considerations. Electrical sensors also may be easy to fabricate (e.g., by photolithographic techniques) and may use a small amount of power for operation. For instance, for the purposes of liquid detection, electrical sensors may act by applying a small constant current or potential across a sensor element (e.g., a resistor, capacitor, and/or conduction gap of the sensor element) and a corresponding output signal may be continually monitored or periodically sampled at a suitable frequency depending upon the particular application. A change in the output may indicate a change in the liquid surrounding the sensor element, thereby detecting when a liquid element of different composition is present and/or at a certain position.

To realize the goal of such a sensor array, individual electrical sensors can be integrated into a large array. A potential difficulty is that as the number of electrical sensors increases, the number of electrical leads to connect the sensors with external power input and signal (e.g., data) output to monitoring equipment may also greatly increase. The increase in electrical leads may make the fabrication and implementation of the sensor array problematic.

The present disclosure describes examples of configurable sensor arrays having high dimensionality fostering the selective detection and positioning of multiple categories of particular agents. The configurable sensor arrays can be used in a variety of applications (e.g., optical sensation and tracking, touch sensation via pressure and/or temperature, etc., acoustics, ambient temperature, deformation, detection of odorants, solvents, and/or solutes, such as in detection and identification of explosives, contraband, drug discovery, biological outgas, medical applications, toxic industrial chemicals, agricultural organics, fugitive emissions, among other applications).

Examples of the present disclosure include systems, devices, and methods for configurable sensor arrays. Such configurable sensor arrays can be used for the applications described in the present disclosure, although the configurable sensor arrays are not limited to such applications. An example of a configurable sensor array includes a plurality of sensors in a matrix array formed on a single backplane and a plurality of elements within one of the plurality of sensors, where the plurality of elements provides alternative electrical paths enabling the one of the plurality of sensors to have a range of output impedances.

FIG. 1 illustrates an example of a passive matrix of a configurable sensor array according to the present disclosure. The example of the passive matrix of the configurable sensor array 100 can comprise one or more gate drivers 102 to supply electrical potential to a plurality of sensors in the sensor array through a plurality of gate lines 104.

In the detailed description of the present disclosure, reference is made to the accompanying drawings that form a part hereof, and in which is shown by way of illustration examples of how the disclosure may be practiced. These examples are described in sufficient detail to enable those of ordinary skill in the art to practice the embodiments of this disclosure, and it is to be understood that other examples may be utilized and that process, electrical, and/or structural changes may be made without departing from the scope of the present disclosure. Further, where appropriate, as used herein, "for example" and "by way of example" should each be understood as an abbreviation for "by way of example and not by way of limitation".

The figures herein follow a numbering convention in which the first digit or digits correspond to the drawing figure number and the remaining digits identify an element or component in the drawing. Similar elements or components between different figures may be identified by the use of similar digits. For example, 104 may reference element "104" in FIG. 1, and a similar element may be referenced as "204" in FIG. 2. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense.

An example of a sensor as described herein is a sensor indicated by the box at 106 in FIG. 1. Interaction by each of the sensors with agents can cause an output impedance of each of the sensors to vary, which can cause variance in an electrical output voltage to be detected as an electronic signal (e.g., data) from each of the plurality of sensors. The electronic output signals can be conducted through a plurality of data lines 108 to a sensor output 109. The sensor output 109 can receive electronic signals (e.g., data) from, for example, the plurality of sensors and process the same for display to a user or transmit the electronic signals to a single readout device for such processing and display to the user.

Consistent with the present disclosure, a variety of electrical sensors may be used, which may have a plurality of elements within each sensor to provide a range of output impedances. Examples include that the plurality of elements comprises at least two elements selected from a group that includes resistive, capacitive, inductive, conductive, and electrochemical sensor elements, among others. All of the plurality of elements within a particular sensor may be of a particular type (e.g., resistive) or various mixtures of element types may be within the particular sensor (e.g., two resistive, one capacitive, and one inductive, among other variations in number and type). The electrical sensors and elements may be alternating current (AC) or direct current (DC), or mixtures thereof. An array can, for example, include 3 sensors through 10,000 sensors or more. An array of sensors can be arranged as a rectangular grid as illustrated in the drawings of the present disclosure. However, an array of sensors may be arranged in any configuration that provides sufficient space to connect the input and output leads to the sensors (e.g., gate lines connected to circuitry of a number of gate drivers and/or data lines connected to circuitry of a number of sensor outputs, respectively). For example, the array of sensors may be arranged in a circle, a spiral pattern, or irregularly. The sensor configuration, however, should be accessible to multiplexed input and output leads, as described in the present disclosure.

A sensor can be created by patterning, for example, a conductive thin-film resistor on a backplane. The resistor may be patterned from a film (e.g., of a metal) by photolithography, among other techniques. As an example, a small potential may be applied across the resistor, which heats up to a particular temperature in proportion to, for example, a temperature coefficient of resistance (TCR) of the particular metal. As conditions around the resistor change (e.g., in response to a particular agent being detected and/or monitored), so too can the thermal conductivity of the sensor, which can also cause an amount of heat transferred away from the resistor to change. As such, the temperature of the resistor can also change, thereby causing the resistance of the resistor to change, and, as a result, the measurable output current of the resistive sensor can also change. Therefore, when a change in the current through a resistor is detected, the change can also signal a change in the amount and/or intensity of the particular agent being monitored by contacting the resistive sensor. Measurable changes in output current from sensors and/or elements thereof of the capacitive, inductive, conductive, and electrochemical types, or mixtures of these types, can similarly be detected.

The configurable sensor arrays described in the present disclosure can, in various examples, combine the sensitivity of passive matrix arrays and/or the selectivity of active matrix arrays, the durability and potentially low cost of electronic components on a single backplane, and configurability to discriminate among a variety of potential agents to be monitored without adding and/or removing the sensors of the array and/or using multiple readout devices.

The circuitry illustrated in FIG. 1 indicates the passive matrix with the plurality of sensors (e.g., sensor 106) directly connected to the gate lines 104 and data lines 108. FIG. 1 also indicates that the passive matrix is positioned (e.g., formed) on a single backplane.

FIG. 2 illustrates an example of a plurality of elements within one of the sensors of a passive matrix of a configurable sensor array according to the present disclosure. FIG. 2 illustrates schematically a magnified view of the sensor 106 shown in FIG. 1. As such, the sensor 206 is connected to a gate line 204 and a data line 208.

By way of example, the sensor 206 illustrated in FIG. 2 can be a resistive sensor that includes a plurality of elements (e.g., subresistors) within the resistive sensor 206. By way of example, the resistive sensor 206 of FIG. 2 shows the plurality of elements (e.g., 212-1 through 212-N) to be six, however the present disclosure is not limited to six elements. That is, the plurality of elements includes any number that is two or more. At least one of the plurality of sensors includes the plurality of elements, however, sensors having the plurality of elements can each have the same or different numbers of elements.

The sensor 206 illustrated in FIG. 2 includes a plurality of sensor select junctions within the sensor 206. The sensor select junctions can be used in a sensor configuration process to select one or more of the plurality of elements (e.g., subresistors) to be operative in the sensor by enabling throughput of the electronic output signal. By way of example, the sensor 206 of FIG. 2 shows the plurality of sensor select junctions (e.g., 215-1 through 215-N) to be six, however the present disclosure is not limited to six sensor select junctions. That is, the plurality of sensor select junctions includes any number that is two or more. Moreover, although the sensor select junctions 215-1 through 215-N are shown by example in FIG. 2 to be between the gate line 204 and each of the plurality of elements 212-1 through 212-N, other examples can position some or all sensor select junctions between the elements and the data line 208.

In some examples, sensor select junctions can be positively selected to enable operability of one or more associated elements (e.g., by being electrically field programmable, using an optoelectric switch, and/or using an antifuse connection, among other means of selection). In addition, in some examples, sensor select junctions can be negatively selected to disable operability of one or more associated resistor elements (e.g., by disconnecting resistor elements, for example with a laser, by being electrically field programmable, using an optoelectric switch, and/or using an antifuse connection, among other means of selection). In various examples, particular sensor select junctions among the plurality of sensor select junctions can be permanently enabled or disabled or can be reversibly enabled or disabled.

That is, in various examples, configuration of sensor arrays can allow dynamic modification of the output voltage range of sensors permanently or reversibly during and/or after manufacture of the sensor arrays. Such modification can be performed by a manufacturer on behalf of a prospective user, based on user-supplied preferences executed by a technician associated with the fabrication, post-fabrication processing, and/or marketing of the configurable sensor arrays, based directly on user input, and/or via instructions executed by a computing device, among others.

A particular element in a sensor of the present disclosure can be formed from a particular material, formed to have a particular area (e.g., width times length), formed to have a particular height, formed to have a particular volume, formed to have a particular length and/or shape (e.g., straight, curved, and/or angular), formed to have a particular structure of internal electrodes (e.g., conductors, among other electrode types) and/or barriers, or a combination of these parameters, among others, in order to have a particular output impedance. In various examples, the output impedance of a particular element can be different from output impedances of other elements in the sensor based on variations in the just-presented parameters. For example, the elements 212-1 through 212-N illustrated in FIG. 2 show variations in some of these parameters in order to vary the output impedances between the gate line 204 and the data line 208.

That is, by way of example, elements 212-1, 212-3, and 212-5 show various electrode configurations that extend within and through a schematic outline of each of the elements and elements 212-2, 212-4, and 212-N show schematic outlines of examples of various shapes of each of the elements, which can also be indicative of different areas, heights, volumes, lengths, etc. Moreover, as described in the present disclosure, one type of sensor material can be used to form a particular element and one or more different types of sensor materials can be used to form others of the plurality of elements in a particular sensor.

Each sensor in the example shown in FIG. 2 includes six elements that have electrical paths that vary the sensor output impedance over multiple orders of magnitude. As such, the various sensors can be selected to utilize the same readout electronics by appropriately configuring appropriate elements in each sensor by enabling and/or disabling particular sensor select junctions. The dynamic connection of various sensor elements can be used to notably increase a detection and/or monitoring range of the configurable sensor arrays described in the present disclosure.

FIG. 3 illustrates an example of an active matrix of a configurable sensor array according to the present disclosure. The example of the active matrix of the configurable sensor array 320 can comprise one or more gate drivers 322 to supply electrical potential to a plurality of sensors in the sensor array through a plurality of gate lines 324. An example of such a sensor is a pixel indicated by the box at 326. Interaction by the pixel 326 with agents can cause an output impedance of the pixel 326 to vary, which can cause variance in an electrical output voltage to be detected as an electronic signal (e.g., data) from each of the plurality of pixels. The electronic output signals can be conducted through a plurality of data lines 328 to a sensor output 329.

The sensor output can receive electronic signals (e.g., data) from the plurality of pixels and process the same for display to a user or transmit the electronic signals to a single readout device for such processing and display to the user.

The circuitry illustrated in FIG. 3 indicates an active matrix 320 with each of the plurality of pixels (e.g., pixel 326) indirectly connected to the gate lines 324 and data lines 328 via a transistor 325. The circuitry illustrated in FIG. 3 indicates an active matrix 320 with a ground line 327 connected thereto. FIG. 3 also indicates that the active matrix is positioned (e.g., formed) on a single backplane.

FIG. 4 illustrates an example of a plurality of elements within one of the sensors of an active matrix of a configurable sensor array according to the present disclosure. FIG. 4 illustrates schematically a magnified view of the pixel 326 shown in FIG. 3. As such, the pixel 426 is connected to a gate line 424, a ground line 427, and a data line 428.

The pixel 426 illustrated in FIG. 4 includes a plurality of elements (e.g., subpixels) within the pixel 426. By way of example, the pixel 426 of FIG. 4 shows the plurality of elements (e.g., 432-1 through 432-N) to be six, however the present disclosure is not limited to six elements. That is, the plurality of elements includes any number that is two or more. At least one of the plurality of pixels includes the plurality of elements, however, pixels having elements can each have the same or different numbers of elements. A transistor 425 as described herein can function as a gate to control electronic access from a gate line through one or more elements to a data line.

The pixel 426 illustrated in FIG. 4 includes a plurality of sensor select junctions within the pixel 426. The sensor select junctions can be used in a sensor configuration process to select one or more of the plurality of elements to be operative in the pixel by enabling throughput of the electronic output signal. By way of example, the pixel 426 of FIG. 4 shows the plurality of sensor select junctions (e.g., 435-1 through 435-N) to be six, however the present disclosure is not limited to six sensor select junctions. That is, the plurality of sensor select junctions includes any number that is two or more. Moreover, although the sensor select junctions 435-1 through 435-N are shown by example in FIG. 4 to be between the gate line 424 and each of the plurality of elements 432-1 through 432-N, other examples can position some or all sensor select junctions between elements and the data line 428.

In accordance with the passive matrix array shown in FIG. 2, in some examples, sensor select junctions shown in the active matrix array shown in FIG. 4 can be positively selected to enable operability of one or more associated elements (e.g., by being electrically field programmable, using an optoelectric switch, and/or using an antifuse connection, among other means of selection). In addition, in some examples, sensor select junctions can be negatively selected to disable operability of one or more associated resistor elements (e.g., by disconnecting resistor elements, for example with a laser, by being electrically field programmable, using an optoelectric switch, and/or using an antifuse connection, among other means of selection). In some examples, particular sensor select junctions among the plurality of sensor select junctions can be permanently enabled or disabled by a user or can be reversibly enabled or disabled by the user. That is, in some examples, configuration of sensor arrays can allow dynamic modification of the output voltage range of sensors permanently or reversibly during and/or after manufacture of the sensor arrays, including based on user-supplied preferences and/or based directly on user input.

In accordance with the passive matrix array shown in FIG. 2, a particular resistor element in a pixel of the present disclosure can be formed from a particular resistor material, formed to have a particular area (e.g., width times length), formed to have a particular height, formed to have a particular volume, formed to have a particular length and/or shape (e.g., straight, curved, and/or angular), formed to have a particular structure of internal electrodes (e.g., conductors, among other electrode types) and/or barriers, or a combination of these parameters, among others, in order to have a particular output impedance. In various examples, the output impedance of the particular element can be different from the output impedance of other resistor elements in the sensor based on variations in the just-presented parameters. For example, the resistor elements 432-1 through 432-N illustrated in FIG. 4 show variations in some of these parameters in order to vary the output impedance from the gate line 424 through the transistor 425 to the data line 428.

That is, by way of example, elements 432-1, 432-3, and 432-5 show various electrode configurations that extend within and through a schematic outline of each of the elements and elements 432-2, 432-4, and 432-N show schematic outlines of examples of various shapes of each of the elements, which can also be indicative of different areas, heights, volumes, lengths, etc. Moreover, as described in the present disclosure, one type of sensor material can be used to form a particular element and one or more different types of sensor materials can be used to form others of the plurality of elements in a particular sensor.

Each pixel in the example shown in FIG. 4 includes six elements that have electrical paths that vary the sensor output impedance over multiple orders of magnitude. As such, the various pixels can be selected to utilize the same readout electronics by appropriately configuring appropriate elements in each pixel by enabling and/or disabling particular sensor select junctions. Additionally, in various examples, integration of pixel level and/or array level circuits can be performed using the same transistor technology used to select particular pixels and/or particular elements within the particular pixels.

Thin-film sensor technologies can have a range of applications, including for detecting and/or monitoring temperature, humidity, light, pressure, magnetism, and chemicals, among other applications. For instance, as-fabricated resistive thin film materials used in thin-film sensors can have resistances that span a wide range of sheet resistance (e.g., from less than 1 $\Omega$/square to greater than 100 million $\Omega$/square). As a result, individually customized sensor electrode configurations and/or custom readout electronics may be used for every sensor depending on its resistance range in a given implementation. Integration of multiple sensors of different types can be accomplished by providing dedicated and customized read-out circuitry for each type of sensor. Production of a custom array with custom readout electronics for each sensor or each group of the particular type of sensor may be expensive per unit unless the product is usable as such, and is purchased, by a large number of downstream customers for the supported application.

However, many potential opportunities for making sensor arrays could involve small volumes, at least initially, and the cost of the custom electronics design and manufacture may represent a substantial risk and/or challenge to the associated technology and/or business of the manufacturer. Accordingly, this approach may be reasonable for small numbers of sensors, however, it may become increasingly complex, cumbersome, and/or costly as the number of sensors and/or types of sensors increases.

There also may be applications where a bandwidth and/or sensitivity of the sensor array is limited by the use of a single sensor and/or electrode design. Accordingly, an ability to change a sensor configuration dynamically may improve performance and/or reduce cost.

An ability to integrate a plurality of (e.g., multiple different) sensor types in large numbers on a single backplane with manageable readout electronics (e.g., a single readout device) can open a range of new applications where sensor data can be spatially and temporally correlated. In addition, matrixed arrays of sensors (e.g., multiplexed) can allow for the reduction of connections to the sensors from 2*M*N to M+N (where M*N=the number of sensors), which can reduce the complexity and/or cost of producing such an array with a large numbers of sensors.

Moreover, for instance, large thin-film transistor (TFT) arrays may be used to control digital x-ray imaging panels. In such an array, a sensor backplane may be designed and optimized for a single specific sensing function, such as x-ray detection, and all pixels may be designed and manufactured to be similar in form and function. Application of such a sensor backplane to a different sensor (e.g., an optical sensor, a temperature sensor, a pressure sensor, etc.) may involve substantial redesign of the system because the system is not configurable or customizable, rather it is carefully optimized and designed for a single sensing function.

In contrast, the present disclosure describes examples of a matrix architecture designed to support a plurality of sensor types in configurable and/or customizable combinations. In various examples, a matrixed sensor array usable for a range of (e.g., multiple) applications can be configured pre- and/or post-fabrication (e.g., by a manufacturer on behalf of a prospective or intended user, and/or by the intended user, among others) to support a range of sensor resistances to enable configurable and reconfigurable (e.g., customizable) use in the range of applications. For example, a series of different elements (e.g., various electrode configurations within patterns formed from different resistor materials, having inter-digitated fingers, having different effective widths, lengths, heights, areas, volumes, shapes, and/or numbers of squares, among other variables) can be formed within each sensor and/or pixel of the matrix and a post-fabrication configuration process can be used to select one or more of the different elements in each pixel that produce a sensor output impedance range which matches a set of readout electronics of a particular single readout device.

The configurable matrix array described in the present disclosure can, in various examples, be formed with active or passive matrix architectures. The passive matrix array may be simpler and/or less expensive to fabricate, but may have issues with cross-talk and/or defect tolerance. An active matrix array may be more expensive and/or complex to fabricate, but may offer better performance and/or durability benefits, including reduced cross-talk, better defect tolerance, a potential for integrated pixel level amplification, and/or integrated row drivers, among other possible benefits relative to the passive matrix array. Although a configurable matrix array may leave portions of a backplane area (e.g., proportional to the number of sensor types and/or impedances supported by different elements) unused for a particular application, such configurable matrix arrays may be fabricated on backplanes using techniques where the cost per unit area is low (e.g., roll-to-roll processes).

FIG. 5 illustrates an example implementation of a plurality of elements within each of a plurality of different types of sensors of an active matrix of a configurable sensor array according to the present disclosure. In accordance with the active matrix arrays illustrated in FIGS. 3 and 4, FIG. 5 illustrates schematically an active matrix of a configurable sensor array 540 that can comprise one or more gate drivers 542 to supply electrical potential to a plurality of sensors in the sensor array through a plurality of gate lines 544.

The circuitry illustrated in FIG. 5 indicates the configurable active matrix 540 where each of a plurality of pixels (e.g., different types of pixels indicated at 549-1 through 549-N) is indirectly connected to the gate lines 544 and data lines 548 via a transistor 545. The circuitry illustrated in FIG. 5 indicates an active matrix 540 with a ground line 547 connected thereto. FIG. 5 also indicates that the active matrix 540 is positioned (e.g., formed) on a single backplane. Electronic output signals of the pixels can be conducted through the plurality of data lines 548 to a sensor output 559. The sensor output can receive electronic signals (e.g., data) from the plurality of pixels and process the same for display to a user, thereby functioning as a single readout device, or transmit the electronic signals to a single readout device for such processing and display to the user.

In accordance with the passive and active matrix arrays illustrated in FIGS. 2 and 4, respectively, each pixel (e.g., of the different types of pixels indicated at 549-1 through 549-N) illustrated in FIG. 5 includes a plurality of sensor select junctions within the pixel (not shown). The sensor select junctions can be used to select one or more of the plurality of elements to be operative in the pixel by enabling throughput of the electronic output signal. By way of example, the different types of pixels indicated at 549-1 through 549-N of FIG. 5 each shows the plurality of elements to be four, however, the present disclosure is not limited to four elements. That is, the plurality of elements includes any number that is two or more.

In accordance with the elements described herein, the configurable active matrix array illustrated in FIG. 5 can be formed with four different element configurations per different type of pixel (e.g., the different types of pixels at 549-1 through 549-N indicated by different shading patterns). For example, in addition to the other element variable described herein, four different sensor materials with differing impedances, such as sheet resistances (e.g., including a platinum temperature sensor with a resistance in the range of a $\Omega/sq$, a carbon nanotube humidity sensor with a resistance in the range of a $k\Omega/sq$, a pressure sensitive rubber with a resistance in the range of a $M\Omega/sq$) covering at least one order of magnitude can be positioned in association with (e.g., deposited on and/or connected to) active matrix array pixels (e.g., the different types of pixels indicated at 549-1 through 549-N).

By way of example, the different types of pixels indicated at 549-1 through 549-N of FIG. 5 show the plurality of pixel types to be four, however, the present disclosure is not limited to four pixel types. That is, the plurality of pixel types includes any number that is two or more. In addition, although FIG. 5 shows a configurable active matrix array, the previously described examples can be applied to a passive matrix array with appropriate modifications.

In various examples, each pixel can be configured by one or more appropriate elements (e.g., subpixels) being selected (e.g., by enabling and/or disabling selected sensor select junctions), for example, depending upon the sheet resistance of the sensor material of that pixel, to provide pixel output impedance values and/or output voltages matched to readout electronics of a single readout device.

Figure 6:
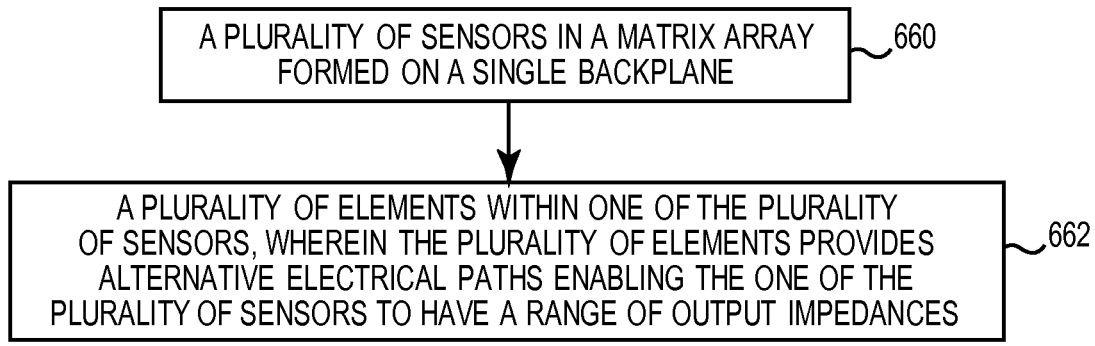
FIG. 6 is a block diagram illustrating an example of a configurable sensor array formed according to the present disclosure.

FIG. 6 is a block diagram illustrating an example of a configurable sensor array formed according to the present disclosure. In accordance with the description of configurable sensor arrays described herein, there is a plurality of sensors formed on a single backplane, as shown in block 660 of FIG. 6. As shown in block 662, there is a plurality of elements within one of the plurality of sensors, where the plurality of elements provides alternative electrical paths enabling the one of the plurality of sensors to have a range of output impedances.

The alternative electrical paths from the plurality of resistor elements can, in various examples, be selectable to have a number of output impedances that provide an electronic signal within a particular voltage range. The matrix array can, in various examples, comprise a matrix array selected from a passive matrix array and an active matrix array. The plurality of sensors can, in various examples, comprise at least two different types of sensors, for example, for detecting at least two different types of agents. The plurality of elements can, in various examples, comprise at least three resistor elements. In addition, the plurality of elements can, in various examples, comprise at least two elements selected from a group that includes resistive, capacitive, inductive, conductive, and electrochemical sensor elements.

In some examples of the present disclosure, a configurable sensor array system can comprise a plurality of thin-film sensors in an active matrix array formed on a single backplane. A plurality of elements can, in various examples, be within each sensor, where the plurality of elements within a particular sensor can provide alternative electrical paths enabling the particular sensor to have a range of output impedances covering at least an ohmic order of magnitude. As such, there can, in various examples, be a number of particular electrical paths from the plurality of elements within each sensor having a number of particular output impedances that are selectable to provide an electronic signal matched to an input range of a single readout device.

In some examples, the plurality of thin-film sensors can comprise at least two different types of thin-film sensors each having differing sheet resistances. In some examples, the plurality of elements can comprise at least two elements each having different output impedances to each provide the alternative electrical paths. In some examples, the at least two elements can comprise thin-film sub-sensors within each sensor each having differing sheet resistances.

A configurable sensor array can be formed by a method according to the present disclosure. Unless explicitly stated, the method examples described herein are not constrained to a particular order or sequence. Additionally, some of the described method examples, or elements thereof, can occur or be performed at the same, or substantially the same, point in time.

As described in the present disclosure, a configurable sensor array can, in various examples, be formed by positioning a plurality of elements within each of a plurality of sensors, where the plurality of elements provides alternative electrical paths enabling each sensor to have a range of output impedances. The configurable sensor array can, in various examples, be formed by positioning the plurality of sensors on a single backplane in a matrix array and selecting a number of particular electrical paths from the plurality of elements having a number of particular output impedances to provide an electronic signal matched to an input range of a single readout device.

Positioning the plurality of elements within each sensor can include positioning at least two elements within each sensor to each provide alternative electrical paths and/or to enable alternative electrical paths between at least two connected elements. Positioning the plurality of sensors on the single backplane in the matrix array can, in various examples, include positioning at least two different types of sensors on the single backplane in the matrix array. As described herein, the matrix array can be formed as selected from a passive matrix array and an active matrix array.

Selecting the number of particular electrical paths from the plurality of elements within each sensor can, in various examples, include selecting for a particular application (e.g., by the manufacturer on behalf of a prospective or intended user, and/or by the intended user, among others) after forming the configurable sensor array. For example, an intended user can choose a particular number of different agents to be detected and/or monitored by the matrix array, which could utilize a number of different sensor types to effectively detect and/or monitor each of the different agents. Each of the different sensor types could have different ranges of output impedances (e.g., that differ by one or more orders of magnitude and/or do not substantially overlap) such that a standard readout device or a single setting of such a readout device may have difficulty in simultaneously detecting electronic signals from the different sensor types (e.g., particular voltage ranges of the electronic signals from the different sensor types) and/or simultaneously displaying the results to the user.

In various examples, the present disclosure describes a configurable (e.g., reconfigurable and customizable) electronics matrix array on a single backplane that enables integration of a plurality of sensor types (e.g., thin-film sensors for detecting at least two different types of agent). Various examples can comprise a thin-film electronics backplane (e.g., passive or active matrix) capable of accommodating a range of sensor types (e.g., thin-film resistive sensors with a range of sheet resistance values of resistor elements incorporated therein). The sensors and/or the elements can be positioned (e.g., formed) on the backplane in any desired pattern (e.g., as selected by an intended user) to provide a configurable (e.g., customized) sensing functionality (e.g., multiple sensing modes, high sampling rates for better statistics, spatial mapping, among other options). Alternatively or in addition, a post-fabrication configuration and/or programming process can be used to modify the configuration of each sensor and/or pixel according to examples described in the present disclosure.

Accordingly, in various examples described in the present disclosure, an intended user and/or a manufacturer on behalf of a prospective user or the intended user can select post-fabrication from a plurality of different sensor types and/or elements (e.g., particular electrical paths) in a matrix array and, as such, the intended user, a technician associated with the fabrication, post-fabrication processing, and/or marketing of the configurable sensor arrays, and/or instructions executed by a computing device, among others, can enable and/or disable a number of elements in the selected sensor types. Enabling and/or disabling the number of elements in the selected sensor types can thereby provide electronic signals from each of the plurality of different sensor types that match an input range of a single readout device. As described herein, selecting for the particular application can include selecting from permanently enabling particular alternative electrical paths and reversibly enabling particular alternative electrical paths among the plurality of elements. Hence, the configurable and reconfigurable design, with capability for post-fabrication customization to serve a variety of applications, can be manufactured in large numbers (e.g., as compared to a pre-fabrication custom design approach), which may result in reduced cost per unit and increased flexibility to develop solutions to a variety of applications that otherwise may have limiting development costs.

Examples of the present disclosure may include configurable sensor arrays, systems, and methods, including executable instructions and/or logic to facilitate configuration or reconfiguration of the sensor arrays. Processing resources can include one or more processors able to access data stored in memory to execute the comparisons, actions, functions, etc., described herein. As used herein, "logic" is an alternative or additional processing resource to execute the comparisons, actions, functions, etc., described herein that includes hardware (e.g., various forms of transistor logic, application specific integrated circuits (ASICs), etc.), as opposed to computer executable instructions (e.g., software, firmware, etc.) stored in memory and executable by a processor.

In a network of computing devices, a number of network devices can be networked together in a Local Area Network (LAN) and/or a Wide Area Network (WAN), a personal area network (PAN), and the Internet, among other networks, via routers, hubs, switches, and the like. As used herein, a network device (e.g., a device having processing and memory resources and/or logic that is connected to a network) can include a number of switches, routers, hubs, bridges, etc.

Figure 7:
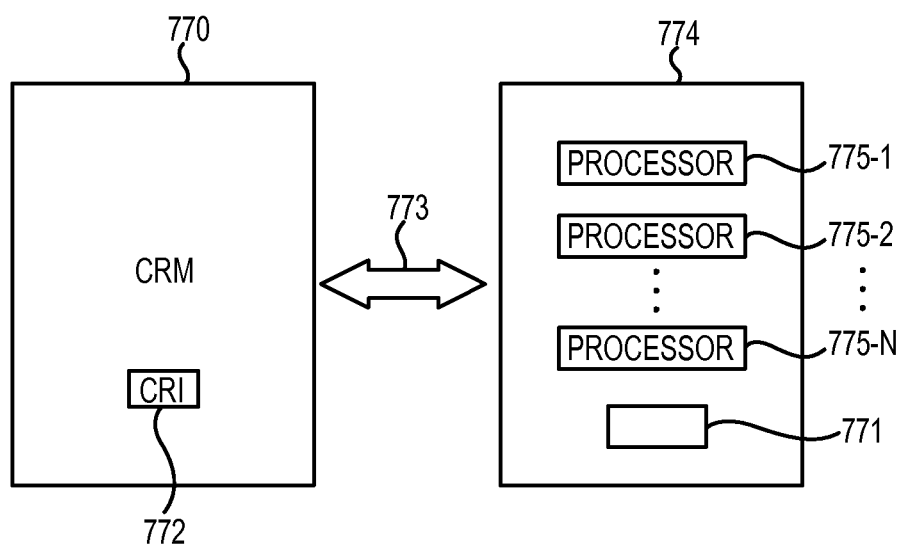
FIG. 7 is a block diagram illustrating an example of a computing device readable medium with processing resources for a configurable sensor array according to the present disclosure.

FIG. 7 is a block diagram illustrating an example of a computing device readable medium (CRM) with processing resources for a configurable sensor array according to the present disclosure. For example, the CRM 770 can be in communication via a communication path 773 with (e.g., operatively coupled to) a computing device 774 having a number of processing resources 775-1, 775-2, . . . , 775-N (e.g., one or more processors). The CRM 770 can include computing device readable instructions (CRI) 772 to cause the computing device 774 to, for example, select one or more of a plurality of sensors in a matrix array formed on a single backplane and enable and/or disable one or more of a plurality of elements within one or more of the plurality of sensors, such that the enabled and/or disabled one or more of the plurality of elements provide alternative electrical paths enabling the one or more of the plurality of sensors to have a range of output impedances. The computing device 774 can also include memory resources 771, and the processing resources 775-1, 775-2, . . . , 775-N can be coupled to these memory resources 771 in addition to those of the CRM 770.

The CRM 770 can be in communication with the computing device 774 having processing resources of more or fewer than 775-1, 775-2, . . . , 775-N. The computing device 774 can be in communication with and/or receive from a tangible non-transitory CRM 770 storing a set of stored CRI 772 executable by one or more of the processing resources 775-1, 775-2, . . . , 775-N for configuration and/or reconfiguration of matrix arrays. The stored CRI 772 can be an installed program or an installation pack. If an installation pack, the memory, for example, can be a memory managed by a server such that the installation pack can be downloaded.

Processing resources 775-1, 775-2, . . . , 775-N can execute the CRI 772 for configuration and/or reconfiguration of matrix arrays. A non-transitory CRM (e.g., CRM 770), as used herein, can include volatile and/or non-volatile memory. Volatile memory can include memory that depends upon power to store information, such as various types of dynamic random access memory (DRAM), among others.

Non-volatile memory can include memory that does not depend upon power to store information. Examples of non-volatile memory can include solid state media such as flash memory, EEPROM, phase change random access memory (PCRAM), magnetic memory such as a hard disk, tape drives, floppy disk, and/or tape memory, optical discs, digital video discs (DVD), Blu-ray discs (BD), compact discs (CD), and/or a solid state drive (SSD), etc., as well as other types of CRM.

The non-transitory CRM 770 can be integral, or communicatively coupled, to a computing device, in either in a wired or wireless manner. For example, the non-transitory CRM 770 can be an internal memory, a portable memory, a portable disk, or a memory located internal to another computing resource (e.g., enabling CRI 772 to be downloaded over the Internet).

The CRM 770 can be in communication with the processing resources 775-1, 775-2, . . . , 775-N via the communication path 773. The communication path 773 can be local or remote to a machine associated with the processing resources 775-1, 775-2, . . . , 775-N. Examples of a local communication path 773 can include an electronic bus internal to a machine such as a computing device where the CRM 770 is one of volatile, non-volatile, fixed, and/or removable storage medium in communication with the processing resources 775-1, 775-2, . . . , 775-N via the electronic bus. Examples of such electronic buses can include Industry Standard Architecture (ISA), Peripheral Component Interconnect (PCI), Advanced Technology Attachment (ATA), Small Computer System Interface (SCSI), Universal Serial Bus (USB), among other types of electronic buses and variants thereof.

The communication path 773 can be such that the CRM 770 is remote from the processing resources 775-1, 775-2, . . . , 775-N such as in the example of a network connection between the CRM 770 and the processing resources 775-1, 775-2, . . . , 775-N. That is, the communication path 773 can be a network connection. Examples of such a network connection can include a LAN, a WAN, a PAN, and the Internet, among others. In such examples, the CRM 770 may be associated with a first computing device and the processing resources 775-1, 775-2, . . . , 775-N may be associated with a second computing device.

It is to be understood that the above description has been made in an illustrative fashion, and not a restrictive one. Although specific examples for devices, systems, methods, computing devices, and instructions have been illustrated and described herein, other equivalent component arrangements, instructions, and/or device logic can be substituted for the specific examples shown herein.

What is claimed:

1. A configurable sensor array, comprising:
   a plurality of sensors in a matrix array formed on a single backplane; and
   a plurality of elements within one of the plurality of sensors, wherein the plurality of elements provides alternative electrical paths enabling the one of the plurality of sensors to have a range of output impedances; and
   wherein at least one of the plurality of elements within the one sensor is formed from a different material selected to provide a different impedance than another of the plurality of elements.

2. The array of claim 1, wherein the alternative electrical paths from the plurality of elements are selectable to have a number of output impedances that provide an electronic signal within a particular voltage range.

3. The array of claim 1, wherein the plurality of sensors comprises at least two different types of sensors.

4. The array of claim 1, wherein the matrix array comprises a matrix array selected from a passive matrix array and an active matrix array.

5. The array of claim 1, wherein the plurality of elements comprises at least two elements selected from a group that includes resistive, capacitive, inductive, conductive, and electrochemical sensor elements.

6. A method of forming a configurable sensor array, comprising:
   positioning a plurality of elements within each of a plurality of sensors, wherein the plurality of elements provides alternative electrical paths enabling each sensor to have a range of output impedances;
   positioning the plurality of sensors on a single backplane in a matrix array; and
   selecting a number of particular electrical paths from the plurality of elements having a number of particular output impedances to provide an electronic signal matched to an input range of a single readout device; and
   wherein at least one of the plurality of elements within one sensor is formed from a different material selected to provide a different impedance than another of the plurality of elements.

7. The method of claim 6, wherein positioning the plurality of elements within each sensor includes positioning at least two elements within each sensor to each provide alternative electrical paths and/or to enable alternative electrical paths between at least two connected elements.

8. The method of claim 6, wherein positioning the plurality of sensors on the single backplane in the matrix array includes positioning at least two different types of sensors on the single backplane in the matrix array.

9. The method of claim 6, wherein the method includes forming the matrix array as selected from a passive matrix array and an active matrix array.

10. The method of claim 6, wherein selecting the number of particular electrical paths from the plurality of elements within each sensor includes selecting for a particular application by a user after forming the configurable sensor array.

11. The method of claim 10, wherein selecting for the particular application includes selecting from permanently enabling particular alternative electrical paths and reversibly enabling particular alternative electrical paths among the plurality of elements.

* * * * *